(12) United States Patent
Amplatz et al.

(10) Patent No.: US 11,944,312 B2
(45) Date of Patent: *Apr. 2, 2024

(54) PERCUTANEOUS CATHETER DIRECTED INTRAVASCULAR OCCLUSION DEVICES

(71) Applicant: St. Jude Medical, Cardiology Division, Inc., St. Paul, MN (US)

(72) Inventors: Kurt Amplatz, North Oaks, MN (US); John C. Oslund, Blaine, MN (US); Xiaoping Gu, Maplewood, MN (US); Matt Glimsdale, St. Michael, MN (US); Daniel O. Adams, Long Lake, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 166 days.

This patent is subject to a terminal disclaimer.

(21) Appl. No.: 17/704,223

(22) Filed: Mar. 25, 2022

(65) Prior Publication Data
US 2022/0211386 A1    Jul. 7, 2022

Related U.S. Application Data

(63) Continuation of application No. 17/193,050, filed on Mar. 5, 2021, now Pat. No. 11,317,920, which is a
(Continued)

(51) Int. Cl.
*A61B 17/12* (2006.01)
*A61B 17/00* (2006.01)

(52) U.S. Cl.
CPC .... *A61B 17/12109* (2013.01); *A61B 17/0057* (2013.01); *A61B 17/12031* (2013.01);
(Continued)

(58) Field of Classification Search
CPC .......... A61B 17/12109; A61B 17/0057; A61B 17/12031; A61B 17/12122;
(Continued)

(56) References Cited

U.S. PATENT DOCUMENTS

| | | |
|---|---|---|
| 3,834,388 A | 9/1974 | Sauer |
| 3,874,388 A | 4/1975 | King et al. |

(Continued)

FOREIGN PATENT DOCUMENTS

| | | |
|---|---|---|
| CN | 1342056 A | 3/2002 |
| CN | 1711978 A | 12/2005 |

(Continued)

OTHER PUBLICATIONS

Japanese Office Action for Application No. 2008331924, dated Mar. 6, 2013.
(Continued)

*Primary Examiner* — Brooke Labranche
(74) *Attorney, Agent, or Firm* — SLEMAN & LUND LLP

(57) ABSTRACT

Embodiments of the present invention provide an improved vascular occlusion device for occlusion of a passageway, cavity, or the like. According to one embodiment, a medical device for occluding a left atrial appendage is provided. The medical device includes a first portion having at least one plane of occlusion that is configured to be positioned outside of the left atrial appendage, and a second portion having at least one plane of occlusion that is configured to be at least partially positioned within a cavity defined by the left atrial appendage.

20 Claims, 8 Drawing Sheets

Related U.S. Application Data continuation of application No. 15/404,454, filed on Jan. 12, 2017, now abandoned, which is a continuation of application No. 11/966,397, filed on Dec. 28, 2007, now abandoned.

(52) U.S. Cl.
CPC .. *A61B 17/12122* (2013.01); *A61B 17/12168* (2013.01); *A61B 17/12172* (2013.01); *A61B 17/12177* (2013.01); *A61B 2017/00575* (2013.01); *A61B 2017/00867* (2013.01); *A61B 2017/12095* (2013.01)

(58) Field of Classification Search
CPC ........ A61B 17/12168; A61B 17/12172; A61B 2017/00575; A61B 2017/00867; A61B 2017/12095
See application file for complete search history.

(56) References Cited

U.S. PATENT DOCUMENTS

| | | | |
|---|---|---|---|
| 4,836,204 A | 6/1989 | Landymore et al. |
| 4,917,089 A | 4/1990 | Sideris |
| 5,064,435 A | 11/1991 | Porter |
| 5,108,420 A | 4/1992 | Marks |
| 5,192,301 A | 3/1993 | Kamiya et al. |
| 5,334,217 A | 8/1994 | Das |
| 5,522,822 A | 6/1996 | Phelps et al. |
| 5,709,707 A | 1/1998 | Lock et al. |
| 5,725,552 A | 3/1998 | Kotula et al. |
| 5,827,325 A | 10/1998 | Landgrebe et al. |
| 5,846,261 A | 12/1998 | Kotula et al. |
| 5,865,791 A | 2/1999 | Whayne et al. |
| 5,944,738 A | 8/1999 | Amplatz et al. |
| 5,984,917 A | 11/1999 | Fleischman et al. |
| 6,123,715 A | 9/2000 | Amplatz |
| 6,132,438 A | 10/2000 | Fleischman et al. |
| 6,152,144 A | 11/2000 | Lesh et al. |
| 6,168,615 B1 | 1/2001 | Ken et al. |
| 6,168,622 B1 | 1/2001 | Mazzocchi |
| 6,368,339 B1 | 4/2002 | Amplatz |
| 6,379,366 B1 | 4/2002 | Fleischman et al. |
| 6,506,204 B2 | 1/2003 | Mazzocchi |
| 6,551,303 B1 | 4/2003 | Van Tassel et al. |
| 6,599,308 B2 | 7/2003 | Amplatz |
| 6,652,555 B1 | 11/2003 | VanTassel et al. |
| 6,652,556 B1 | 11/2003 | VanTassel et al. |
| 6,682,546 B2 | 1/2004 | Amplatz |
| 6,730,108 B2 | 5/2004 | Van Tassel et al. |
| 6,830,576 B2 | 12/2004 | Fleischman et al. |
| 6,911,037 B2 | 6/2005 | Gainor et al. |
| 6,949,113 B2 | 9/2005 | Van Tassel et al. |
| 7,044,134 B2 | 5/2006 | Khairkhahan et al. |
| 7,122,043 B2 | 10/2006 | Greenhalgh et al. |
| 7,128,073 B1 | 10/2006 | van der Burg et al. |
| 7,152,605 B2 | 12/2006 | Khairkhahan et al. |
| 7,169,164 B2 | 1/2007 | Borillo et al. |
| 7,192,439 B2 | 3/2007 | Khairkhahan et al. |
| 7,762,943 B2 | 7/2010 | Khairkhahan |
| 8,034,061 B2 | 10/2011 | Amplatz et al. |
| 8,657,873 B2 | 2/2014 | Khairkhahan et al. |
| 2001/0031981 A1 | 10/2001 | Evans et al. |
| 2002/0111647 A1 | 8/2002 | Khairkhahan et al. |
| 2003/0057156 A1 | 3/2003 | Peterson et al. |
| 2003/0074019 A1 | 4/2003 | Gray et al. |
| 2003/0199819 A1 | 10/2003 | Beck |
| 2003/0199923 A1 | 10/2003 | Khairkhahan et al. |
| 2003/0212432 A1 | 11/2003 | Khairkhahan et al. |
| 2004/0044361 A1 | 3/2004 | Frazier et al. |
| 2004/0073242 A1 | 4/2004 | Chanduszko |
| 2005/0033321 A1 | 2/2005 | Fleischman et al. |
| 2005/0070952 A1 | 3/2005 | Devellian |
| 2005/0228434 A1 | 10/2005 | Amplatz et al. |
| 2006/0074410 A1 | 4/2006 | Malecki et al. |
| 2006/0106419 A1 | 5/2006 | Gingras |
| 2006/0122645 A1 | 6/2006 | Brady et al. |
| 2006/0136043 A1 | 6/2006 | Cully et al. |
| 2006/0241690 A1 | 10/2006 | Amplatz et al. |
| 2006/0247680 A1 | 11/2006 | Amplatz et al. |
| 2006/0253129 A1 | 11/2006 | Liddicoat et al. |
| 2006/0266474 A1 | 11/2006 | Burnside et al. |
| 2007/0043391 A1 | 2/2007 | Moszner et al. |
| 2007/0083230 A1 | 4/2007 | Javois |
| 2007/0112380 A1 | 5/2007 | Figulla et al. |
| 2007/0112381 A1 | 5/2007 | Figulla et al. |
| 2007/0167980 A1 | 7/2007 | Figulla et al. |
| 2007/0168019 A1 | 7/2007 | Amplatz et al. |
| 2007/0265656 A1 | 11/2007 | Amplatz et al. |
| 2007/0270891 A1 | 11/2007 | McGuckin |
| 2008/0065156 A1 | 3/2008 | Hauser et al. |
| 2008/0082132 A1 | 4/2008 | Annest et al. |
| 2008/0200945 A1 | 8/2008 | Amplatz et al. |
| 2008/0262518 A1 | 10/2008 | Freudenthal |
| 2009/0018562 A1 | 1/2009 | Amplatz et al. |

FOREIGN PATENT DOCUMENTS

| | | |
|---|---|---|
| CN | 1799521 A | 7/2006 |
| DE | 10338702 B3 | 3/2005 |
| DE | 102005053957 A1 | 5/2007 |
| JP | 2003512128 A | 4/2003 |
| JP | 2007504888 A | 3/2007 |
| WO | 9731672 A1 | 9/1997 |
| WO | 2002071977 A2 | 9/2002 |
| WO | 2007140797 A1 | 12/2007 |
| WO | 2008040555 A2 | 4/2008 |

OTHER PUBLICATIONS

International Search Report for PCT/US08/86601 dated Apr. 13, 2009; 3 pages.

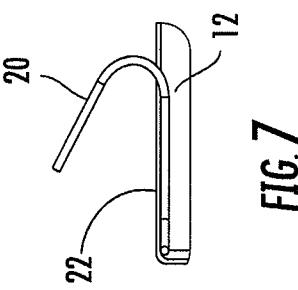
FIG. 7
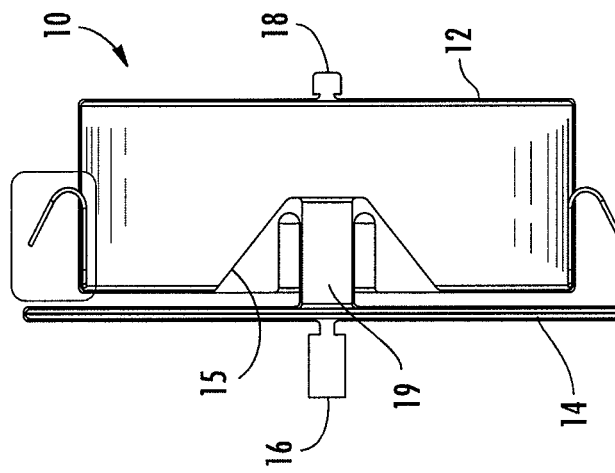
FIG. 6
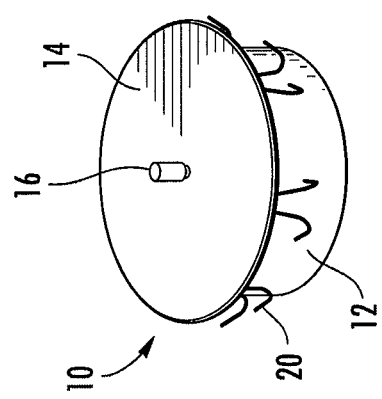
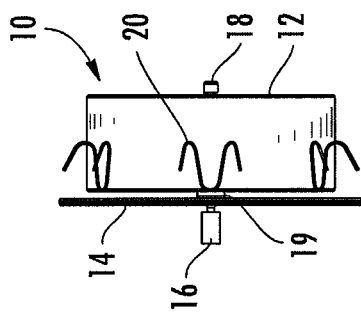
FIG. 5
FIG. 4

PERCUTANEOUS CATHETER DIRECTED INTRAVASCULAR OCCLUSION DEVICES

CROSS-REFERENCE TO RELATED APPLICATIONS

This application is a continuation of U.S. patent application Ser. No. 17/193,050, filed Mar. 5, 2021, which is a continuation of U.S. patent application Ser. No. 15/404,454, filed Jan. 12, 2017, which is a continuation of U.S. patent application Ser. No. 11/966,397, filed Dec. 28, 2007, the disclosures of which are both hereby incorporated by reference herein.

BACKGROUND OF THE INVENTION

1. Field of the Invention

The present invention generally relates to intravascular devices for treating certain medical conditions and, more particularly, relates to intravascular occlusion devices for selective occlusion of a vessel, chamber, channel, hole, cavity, or the like, anywhere in the body's circulatory system where it is desired to stop the flow of blood. The devices made in accordance with the invention are particularly well suited for delivery through a catheter or the like to a remote location in a patient's vascular system within a patient's body whereby a passageway, cavity, or the like is to be occluded.

II. Description of the Related Art

A wide variety of intravascular devices are used in various medical procedures. Certain intravascular devices, such as catheters and guidewires, are generally used simply to deliver fluids or other medical devices to specific locations within a patient's body, such as a selective site within the vascular system. Other, frequently more complex, devices are used in treating specific conditions, such as devices used in removing vascular occlusions or for treating septal defects and the like.

In certain circumstances, it may be necessary to occlude a patient's vessel, chamber, channel, hole, cavity, or the like such as to stop blood flow therethrough. For example, atrial fibrillation may result in the formation of a blood clot in the left atrial appendage (LAA), which may become dislodged and enter the blood stream. By occluding the LAA, the release of blood clots from the LAA may be significantly reduced, if not eliminated. Various techniques have been developed to occlude the LAA. For instance, balloon-like devices have been developed that are configured to be implanted completely within the cavity of the LAA, while surgical techniques have also been developed where the cavity of the LAA is inverted and surgically closed.

Despite these techniques for occluding the LAA, it would be advantageous to provide an improved occlusion device which offers increased flexibility, improved retention, and improved thrombogenicity within a vessel, chamber, channel, hole, cavity, or the like.

SUMMARY OF THE INVENTION

The present invention is well suited for the selective occlusion of a vessel, lumen, channel, hole, cavity, or the like, such as a Patent Ductus Arteriosus (hereinafter PDA), an Atrial Septal Defect (herein after ASD), a Ventricular Septal Defect (herein after VSD), an arterial venous fistula (AVF), an arterial venous malformation (AVM), or the left atrial appendage (LAA).

According to one embodiment, a medical device for occluding a LAA is provided. The medical device includes a first portion having at least one plane of occlusion that is configured to be positioned outside of the LAA, and a second portion having at least one plane of occlusion that is configured to be at least partially positioned within a cavity defined by the LAA. For example, the planes of occlusion may comprise metal, polyester, other bio-compatible polymers, or a combination thereof.

According to various aspects, the medical device may include a first portion (e.g., a disk portion) having a first diameter and a second portion (e.g., a cylindrical portion) having a second diameter. The medical device may also include a transition segment coupling the first portion and the second portion and configured to provide flexibility therebetween, wherein the transition segment has a transition diameter substantially smaller than the first and second diameters. The second portion may have a second diameter smaller than the first diameter. Furthermore, the ratio of the first diameter to the third diameter may be about 6 to 4.5, the ratio of the second diameter to the third diameter may be about 2 to 4, and/or the first diameter may be at least about 10% larger than the second diameter. Moreover, the medical device may include a third portion coupled to, and extending distally from, the second portion, wherein the third portion has a third diameter smaller than the second diameter. The first, second, and third portions may be configured to be constrained to a smaller diameter than the expanded preset configuration for delivery to the LAA and to self expand when unconstrained.

According to one embodiment of the medical device, the medical device includes at least one layer of occluding material having a plurality of woven metallic strands (e.g., Nitinol). The medical device could also include a plurality of hooks extending from the second portion and configured to engage the cavity defined within the LAA. The plurality of hooks may have barbs. The medical device may include a transition segment coupling the first portion and the second portion that is configured to provide flexibility therebetween, and the first portion may be configured to flex up to about 30 degrees with respect to the second portion along a central axis extending through the first and second portions. The medical device may be configured to be constrained within a catheter having an outer diameter of less than about 11, 10, or 9 French. In addition, medical device maybe configured to extend to a depth of about 20, 15, or 10 mm or less within the cavity defined by the LAA. According to one embodiment of the present invention, the medical device may be configured to occlude at least a portion of the LAA in less than about 10, 5, 4, 3, or 2 minutes, with observed occlusions in testing as low as within 1 minute. The medical device may also include an occluding material retained within the first portion and/or the second portion. The occluding material may be in the shape of a disk or surface extending across the interior of the cavity and/or extending over the opening to the cavity. The occluding material may be retained to the at least one layer of woven metal strands. Furthermore, the medical device may be configured to be delivered over a guidewire.

An additional embodiment of the present invention provides a method for occluding a LAA with a medical device. The method includes constraining a medical device at a smaller diameter than an expanded preset configuration, wherein the medical device comprises a first portion having at least one plane of occlusion and a second portion having at least one plane of occlusion. The method also includes delivering the medical device proximate to the LAA and deploying the medical device such that the first portion expands and is positioned outside of the LAA and the second portion expands outwardly to engage at least a portion of the cavity within the LAA.

Various aspects of the method include constraining the medical device within a catheter, wherein deploying comprises retracting the catheter relative to the medical device. The method may further include advancing the catheter distally following the deploying step so as to constrain the medical device within the catheter. The constraining step may include stretching the medical device along a longitudinal axis thereof to the smaller diameter. The deploying step may include deploying the medical device such that the first portion overlies an opening of the LAA. The method may additionally include piercing the heart prior to delivering the medical device proximate to the LAA. The deploying step may further include unscrewing a delivery system threadably coupled to the medical device. Furthermore, the method may include repositioning the medical device within a catheter following deployment of the medical device from the catheter. Additionally, the method may include imaging the LAA using two dimensional intracardiac echocardiography, angiography, magnetic resonance imaging, transesphogeal echocardiograpy, and/or Doppler color flow mapping. The delivering step may include delivering the medical device over a guidewire. Another aspect of the method may further include verification of LAA occlusion by injection of radiopaque contrast media through the catheter, into the left atrium adjacent the deployed medical device and observing, via angiograghy, whether contrast enters the cavity defined by the LAA and further whether any contrast that may have entered the cavity is stagnant, wherein both observations indicate occlusion of the LAA. Additionally, the method may include repositioning the medical device following unsuccessful occlusion of the LAA by contrast observation.

An alternative method of deployment may include the step of positioning the distal end of the catheter within the left atrium and outside the opening of the LAA cavity, proximally retracting the catheter relative to the device, to partially deploy the second portion of the medical device within the left atrium, advancing distally the catheter and device to insert the second portion at least partially into the cavity, and deploying the remainder of the device by further proximal retraction of the catheter relative to the device.

An additional embodiment of the present invention provides a delivery assembly for delivering a medical device for occluding a LAA. The delivery assembly includes a delivery device coupled to the medical device, wherein the medical device comprises at least one plane of occlusion configured to be positioned outside of the LAA and at least one plane of occlusion configured to be at least partially positioned within a cavity defined by the LAA. The delivery assembly also includes a catheter configured to overlie the delivery device and constrain the medical device therein, wherein the catheter is axially displaceable relative to the delivery device.

Various aspects of the delivery assembly include a medical device having a plurality of planes of occlusion positioned outside of the LAA and within the cavity defined by the LAA. In addition, at least one plane of occlusion may be configured to overlie an opening of the LAA. The catheter may have an outer diameter of less than about 11 French. The delivery device and catheter may be configured to be delivered to the left atrial appendage with a guide wire.

Furthermore, the catheter may be axially displaceable relative to the delivery device such that the medical device is configured to be deployed from the catheter in response to displacement of the catheter with respect to the delivery device. The medical device may be configured to be recaptured within the catheter in response to displacement of the catheter with respect to the delivery device.

The occlusion device may provide several advantages. For example, the device may be smaller than conventional occlusion devices, not only in a constrained diameter for delivery to the LAA, but also the depth that the device extends within the cavity of the LAA. The smaller depth that the device extends within the cavity of the LAA may also allow the device to be more easily positioned and implanted therein. In addition, because the device may be smaller, the delivery device may also be smaller, such that the likelihood of injuring the tissue when delivering the device is reduced, and the device may be delivered quicker since the delivery device should be able to be more easily maneuvered within the vasculature. Moreover, the articulation and flexibility of the device and delivery system may improve the ability to bend around corners within the vasculature when delivering the device. The device is also repositionable, as the device may be retracted back within the catheter following deployment of the device. The device may also include a plurality of occluding layers or planes, which may not only improve the thrombogencity of the device, but also eliminate the need to include additional occlusion techniques, such as adding layers of polyester to the device. For example, according to one embodiment the device is capable of occluding the LAA in less than about 10 minutes and even less than about 5 minutes. The device may also result in lower complications, such as embolizations, shunts, and effusion. Furthermore, the device may be delivered over-the-wire, and visualization techniques, such as intracardiac echocardiography ("ICE") may be used to properly size the LAA before implanting the device and during the implantation procedure.

BRIEF DESCRIPTION OF THE DRAWINGS

Figure 1A:
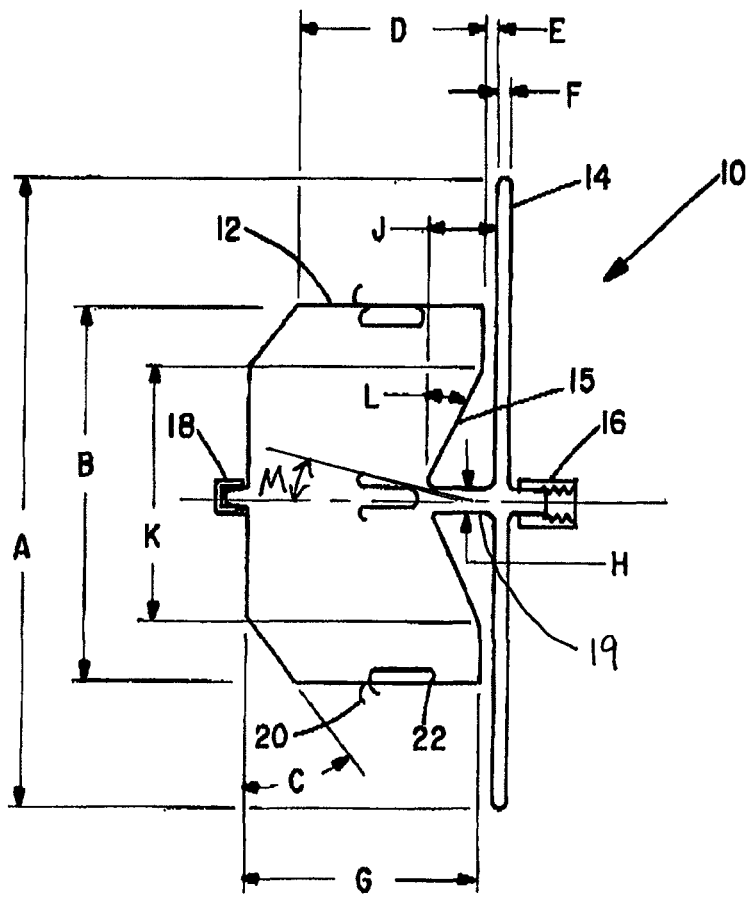
Figure 1B:
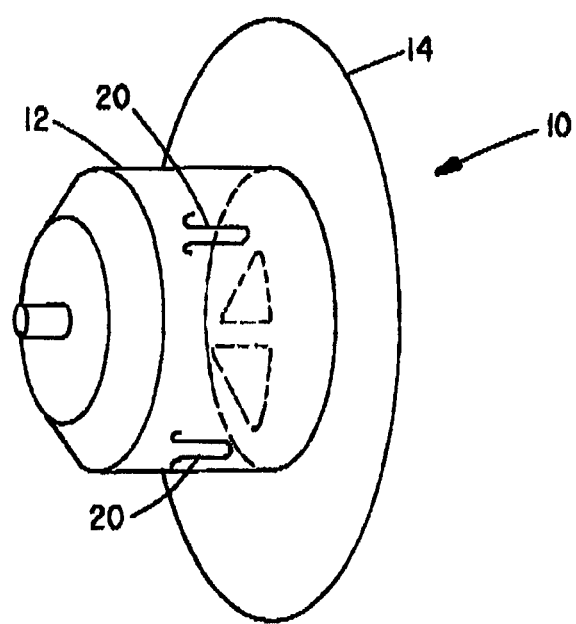
Figure 2:
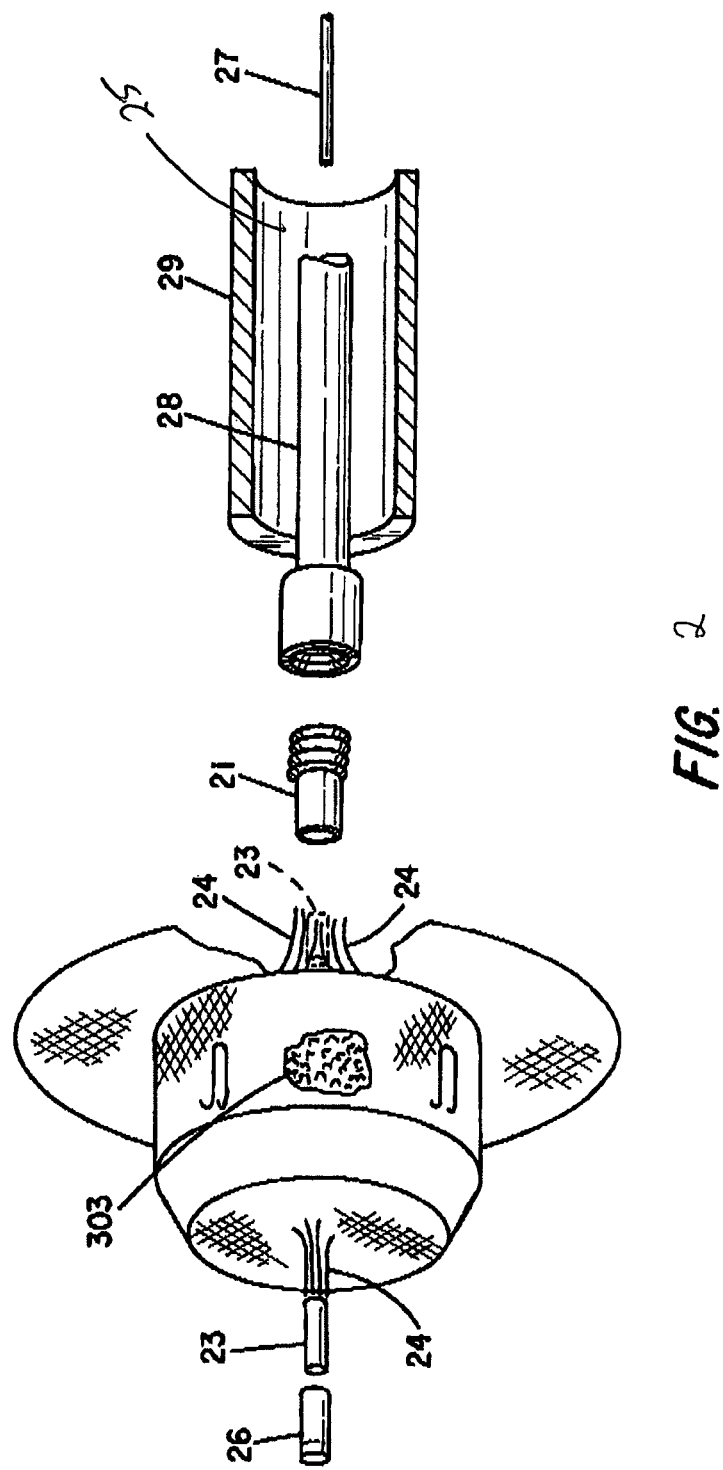
Figure 3A:
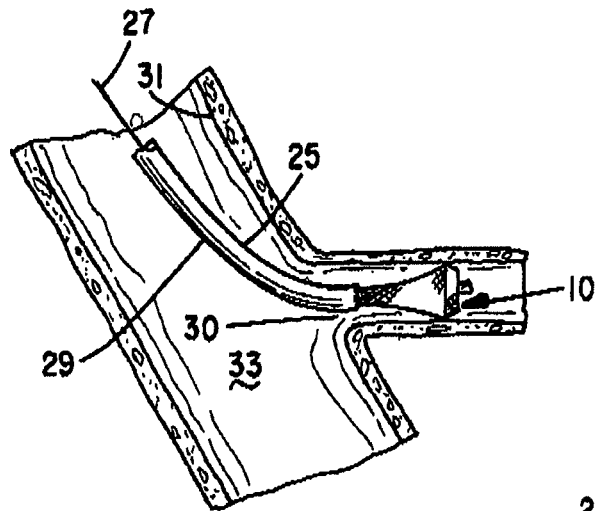
Figure 3B:
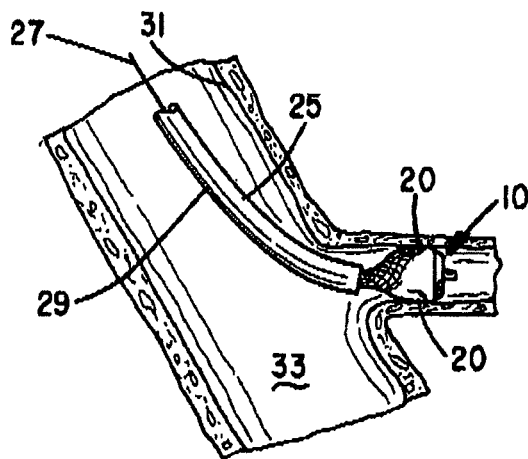
Figure 3C:
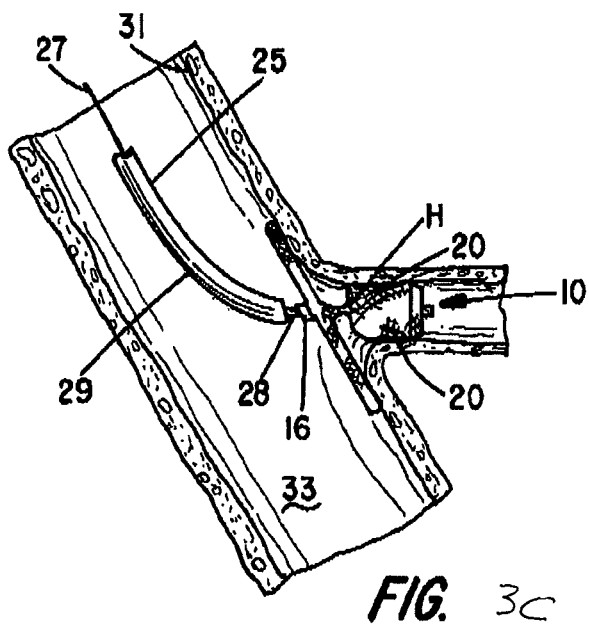
Figure 8:
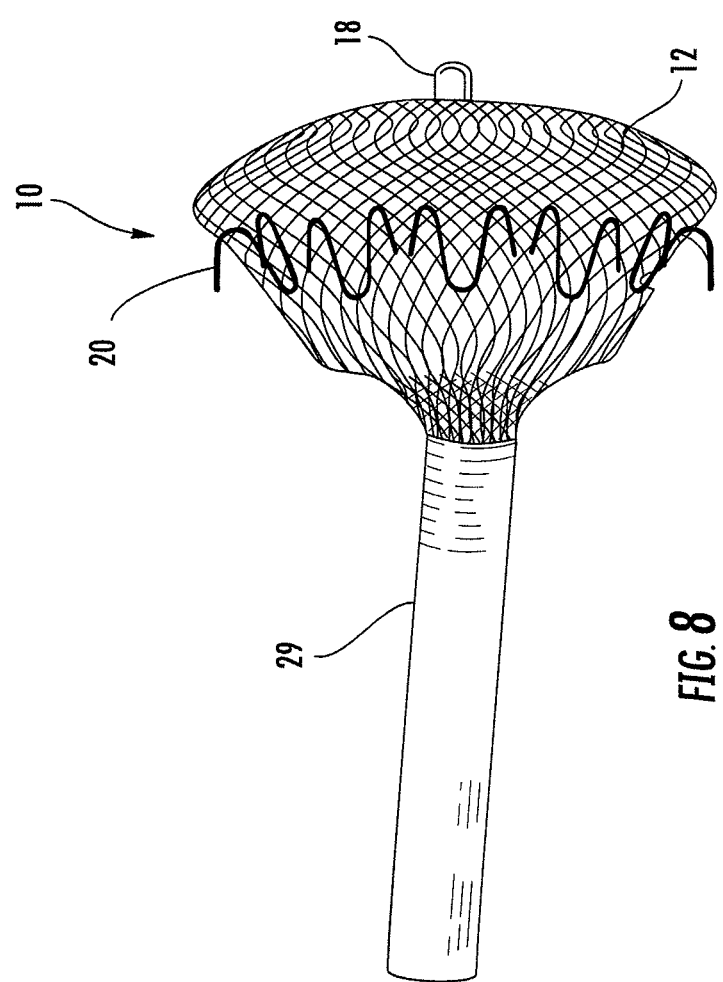
Figure 9:
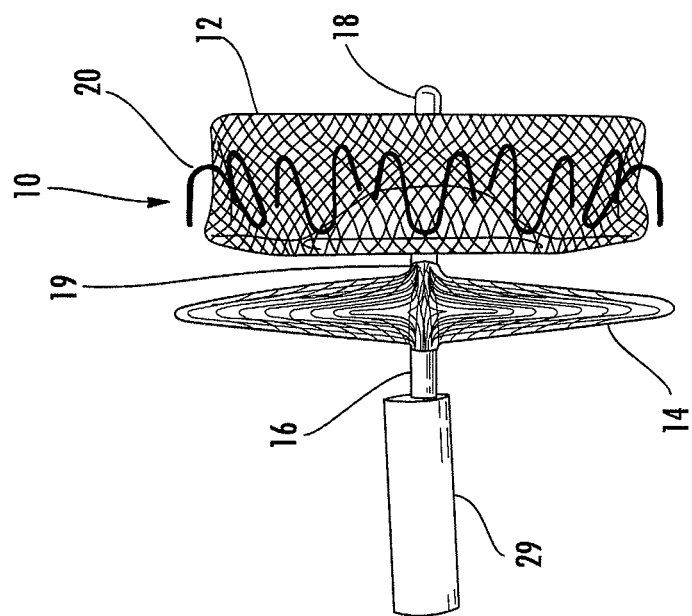
Figure 10:
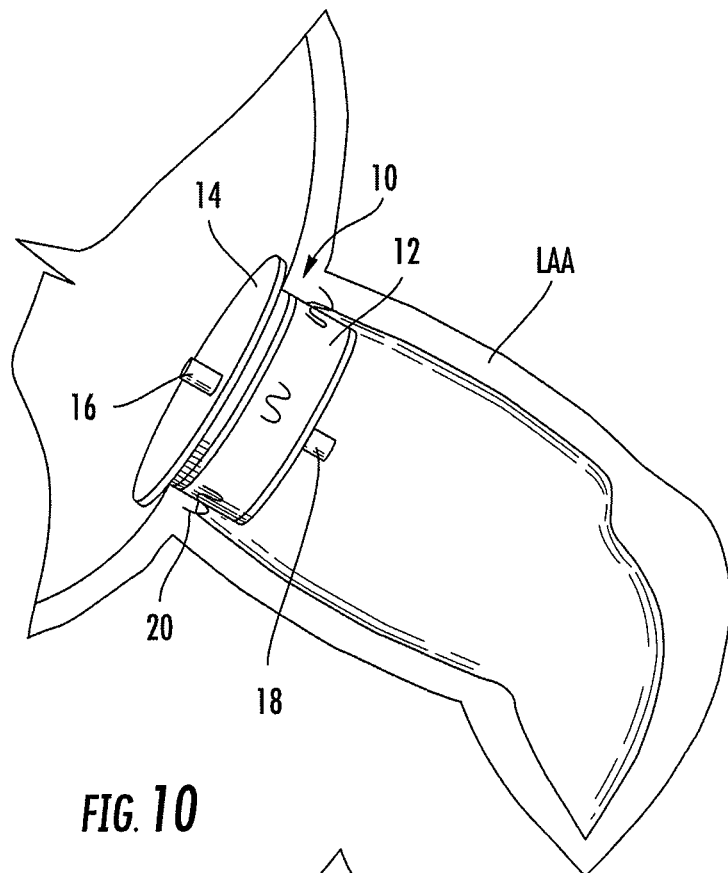
Figure 11:
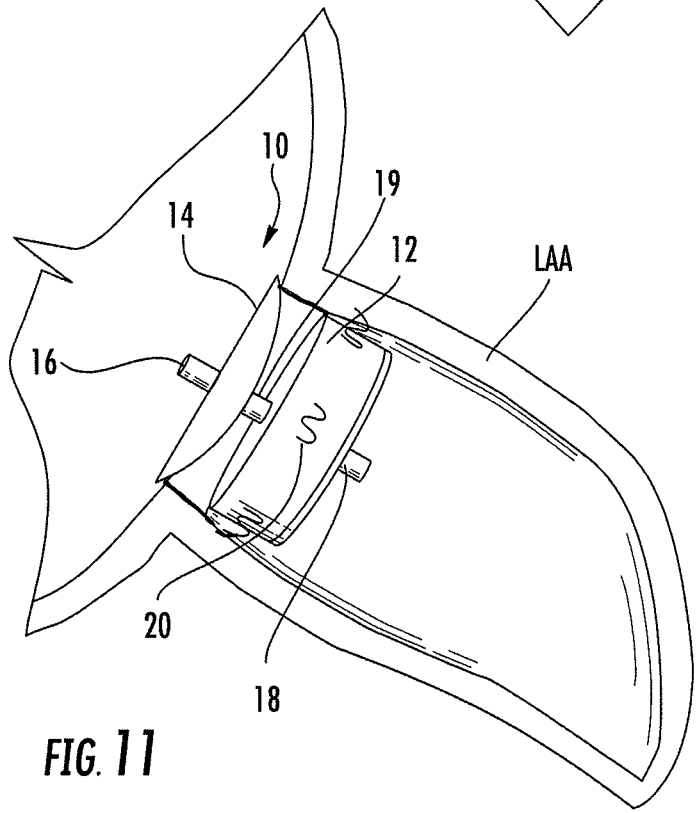

Having thus described the invention in general terms, reference will now be made to the accompanying drawings, which are not necessarily drawn to scale, and wherein:

FIG. 1A is a cross-sectional view of an occlusion device in accordance with one embodiment of the present invention;

FIG. 1B is a perspective view of the device of FIG. 1A;

FIG. 2 is a partially exploded assembly view of an alternative single disk device and delivery apparatus according to one embodiment of the present invention;

FIGS. 3A through 3C depict progressive stages of deployment of the device of FIGS. 1A and 1B;

FIG. 4 is a perspective view of an occlusion device for occluding the LAA according to one embodiment of the present invention;

FIG. 5 is a side elevational view of the occlusion device shown in FIG. 4;

FIG. 6 is a cross-sectional view of the occlusion device shown in FIG. 4;

FIG. 7 is an enlarged partial side view of the occlusion device shown in FIG. 4 illustrating a hook;

FIGS. 8 and 9 are perspective views of a an occlusion device being deployed according to one embodiment of the present invention;

FIG. 10 is a perspective view of an occlusion device deployed in the LAA according to an embodiment of the present invention; and FIG. 11 is a perspective view of an occlusion device deployed in the LAA according to another embodiment of the present invention.

DETAILED DESCRIPTION OF THE PREFERRED EMBODIMENTS

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Embodiments of the present invention may provide an improved percutaneous catheter directed intravascular occlusion device 10 for use in the vasculature in patients' bodies, such as blood vessels, channels, lumens, a hole through tissue, cavities, and the like. Other physiologic conditions in the body occur where it is also desirous to occlude a vessel or other passageway to prevent blood flow into or therethrough. These device embodiments may be used anywhere in the vasculature where the anatomical conditions are appropriate for the design.

According to one embodiment of the present invention for forming a medical device 10 of the invention, a metal fabric is formed of a plurality of wire strands having a predetermined relative orientation with respect to one another. However, it is understood that according to additional embodiments of the present invention, the device 10 may be formed using various techniques. For example, the device 10 could be etched or laser cut from a tube such as to form an interstice geometry, or the device could comprise an occlusion material coupled to a scaffolding structure or a plurality of slices of a tubular member coupled together, such as via gluing. Moreover, it is understood that the device 10 may comprise one or more layers of occluding material such that the device may be a variety of occluding materials capable of at least partially inhibiting blood flow therethrough in order to facilitate the formation of thrombus.

Although the term "strand" is discussed herein, "strand" is not meant to be limiting, as it is understood the fabric may comprise one or more wires, cords, fibers, yarns, filaments, cables, threads, or the like, such that such terms may be used interchangeably.

According to one embodiment, the occluding material is a metal fabric including a plurality of strands, such as two sets of essentially parallel generally helical strands, with the strands of one set having a "hand", i.e., a direction of rotation, opposite that of the other set. The strands may be braided, interwoven, or otherwise combined to define a generally tubular fabric.

The pitch of the strands (i.e., the angle defined between the turns of the strands and the axis of the braid) and the pick of the fabric (i.e., the number of wire strand crossovers per unit length) may be adjusted as desired for a particular application. The wire strands of the metal fabric used in one embodiment of the present method may be formed of a material that is both resilient and can be heat treated to substantially set a desired shape. Materials which may be suitable for this purpose include a cobalt-based low thermal expansion alloy referred to in the field as Elgiloy, nickel-based high temperature high-strength "superalloys" commercially available from Haynes International under the trade name Hastelloy, nickel-based heat treatable alloys sold under the name Incoloy by International Nickel, and a number of different grades of stainless steel. The important factor in choosing a suitable material for the wires strands is that the wires retain a suitable amount of the deformation induced by the molding surface (as described below) when subjected to a predetermined heat treatment and elastically return to said molded shape after substantial deformation.

One class of materials which meets these qualifications is so-called shape memory alloys. One particularly preferred shape memory alloy for use in the present method is Nitinol. NiTi alloys are also very elastic—they are said to be "superelastic" or "pseudoelastic". This elasticity may allow the device to return to a preset expanded configuration for deployment following passage in a distorted form through a delivery catheter. Moreover, other suitable materials include those that are compatible with magnetic resonance imaging (MRI), as some materials may cause heat or torque resulting from performing MRI, and some materials may distort the MRI image. Thus, metallic and/or non-metallic materials that reduce or eliminate these potential problems resulting from using MRI may be employed.

In forming a medical device according to one embodiment of the present invention, an appropriately sized piece of the fabric is cut from the larger piece of fabric which is formed, for example, by braiding wire strands to form a long tubular braid. When cutting the fabric to the desired dimensions, care should be taken to ensure that the fabric will not unravel. One can solder, braze, weld, coat, glue, clamp, tie or otherwise affix the ends of the desired length together (e.g., with a biocompatible cementitious organic material).

Furthermore, one or more layers of fabric may be employed to form a medical device. For example, two layers of metal fabric could be separately woven into tubular members, with one tubular member coaxially disposed within the second tubular member. For further discussion regarding a multi-layer braided device and techniques for fabricating such a device, see U.S. Patent Appl. Publ. No. 2007/0168019 to Amplatz et al., which is hereby incorporated in its entirety by reference.

The tubular braid used to fabricate occlusion devices according to one embodiment of the present invention may range from wire having a diameter of 0.0015 to 0.005 in., preferably in the range of 0.003 to 0.0045 in. The number of wires in the tubular braid may vary from 36 to 144 but preferably is in the range of 72 to 144. The pick count of the braid may vary from 30 to 100. The fabric having an average area between supporting fibers 0.0016 sq cm. and 0.25 sq cm.

Once an appropriately sized piece of the metal fabric is obtained, the fabric is deformed to generally conform to a surface of a molding element. Deforming the fabric will reorient the relative positions of the wire strands of the metal fabric from their initial order to a second, reoriented configuration. The shape of the molding element should be selected to deform the fabric into substantially the shape of the desired medical device when unconstrained. Once the molding element is assembled with the metal fabric generally conforming to a molding surface of that element, the fabric can be subjected to a heat treatment while it remains in contact with that molding surface. After the heat treatment, the fabric is removed from contact with the molding element and will substantially retain its shape in a deformed state.

FIGS. 1A and 1B illustrate an embodiment of a medical device 10 in accordance with one embodiment of the present invention. The device 10 has a generally cylindrical body portion 12 and an outwardly extending forward disk end 14.

The body portion 12 is sized to be somewhat larger (e.g., about 10-30%), than the vessel to be occluded. This sizing is intended to provide one element of anchoring the device to prevent dislodgement. The disk portion 14 of the device 10 is intended to abut the adjacent wall surrounding the aperture, to prevent device movement toward the body portion direction and to assist in sealing the aperture. According to one embodiment, the disk portion 14 is oversized so as to be capable of overlying the ostium or opening of the LAA and lying adjacent to, and in flush contact with, the wall of the atrium, as shown in FIGS. 10 and 11. The disk portion 14 may also be flexible so as to be capable of conforming to the curvature of the wall of the atrium. The disk portion 14 may be various sizes and configurations, such as a flat disk as shown in FIGS. 1A, 1B, 4, and 10, or a disk having a convex distal end as shown in FIG. 11. The disk portion 14 may have a depth or thickness depending on the thickness and number of layers employed, although the depth should be minimized due to the possibility of clot formation around the disk portion and a reduced volume within the atrium.

The body portion 12 may be oversized so that it will engage the lumen of the vessel, body organ, or the like to be occluded. The device 10 may then be held in place by the combination of the radial engagement between the body portion and the lumen of the vessel, body organ, or the like and the hooks 20 which engage the wall. Over a relatively short period of time, thrombi will form in and on the device 10 and occlude the lumen. Although the body portion 12 and disk portion 14 may be various sizes, the disk portion may be at least about 10% larger in diameter than the body portion according to one embodiment.

For example, FIG. 10 illustrates the occlusion device 10 implanted within the LAA. The occlusion device 10 is positioned such that the disk portion 14 overlies the ostium of the LAA, while the body portion 12 is positioned within the LAA. Thus, the disk portion 14 ensures that the body portion 12 is implanted to a predetermined depth within the LAA. The body portion 12 is sized and configured to self expand and engage the wall of the LAA, and the hooks 20 are configured to penetrate into the wall of the LAA, as explained below. Over time, thrombi will form in and on the disk 14 and body portion 12 to occlude the LAA.

Those skilled in the art will appreciate that in order to speed up the occlusion of the vessel device, the device may be coated with a suitable thrombogenic agent, filled with a polyester fiber, braided with an increased number of wire strands, or include multiple layers of fabric. For example, the device 10 may include one or more layers of polyester fiber positioned within the body portion 12 and/or the disk portion 14. In particular, a layer of polyester fiber may be sized and configured to be positioned within each of the body portion 12 and disk portion 14 and sutured circumferentially about its periphery and about the inner circumference of the body portion and disk portion, respectively. The polyester fiber is flexible and may be easily collapsed with the device 10 for delivery through a catheter. The interwoven fiber may attach to a clot to retain the clot firmly within the device as it forms the occlusion.

Therefore, the device 10 may include a plurality of planes of occlusion. A plane of occlusion may be any surface, whether flat or irregular in shape, that may be oriented generally transverse to the flow of blood so as to facilitate the formation of thrombus. For example, the body portion 12 and disk portion 14 may include at least one plane of occlusion, such as each surface or layer of the disk portion and each surface or layer of the body portion. Moreover, additional layers of fabric and/or each layer of polyester fiber within the disk portion and/or body portion may add additional planes of occlusion. Furthermore, the one or more of planes of occlusion associated with the disk portion 14 may be positioned to overlie the ostium of the LAA, while the one or more planes of occlusion associated with the body portion 12 may be positioned within the cavity defined by the LAA. According to one embodiment of the present invention, the first portion and second portion of the device 10 are configured to occlude at least a portion of the LAA in less than about 10 minutes and even less than 5 minutes with observed occlusions in testing as low as within 1 minute.

The device 10 includes a transition segment 19 having a diameter H, between the body portion 12 and the disk portion 14 that is substantially smaller in diameter than the cylindrical diameter B and the disk diameter A. This small transition diameter allows the disk portion to easily orient itself to the vessel wall containing the aperture where the wall is not truly perpendicular. According to one embodiment the body portion 12 is capable of flexing to an angle M of up to about 30 degrees about the transition segment 19 as shown in FIG. 1A. Additionally, the recessed transition diameter H within an indentation 15 in the end of the body member 12 may allow the device to conform to the anatomy in which the device is being positioned by acting like a spring member for maintaining axial tension between the disk and the cylindrical body. Separation between the disk and the cylindrical body may not impact device performance.

As shown in FIGS. 1A, 1B, and 7, the device 10 may include retention hooks 20. The retention hooks 20 may be fabricated from Nitinol wire that is heat set into a hook shape at each end and has a bend, e.g., a bend of less than about 180 degrees, in the mid length segment of the wire to create 2 interconnected hooks. The hooks 20 may also extend within the device 10 as shown in FIG. 7. The ends of the hooks are oriented toward the disk and may be sutured or fastened by any known means to the braided fabric on the body portion 12 of the device. According to one embodiment, the wires of the hooks 20 may be about 0.003-0.007 inches in diameter and 2-10 mm in length and flexible enough to be back loaded into the delivery catheter or forward loaded, if introduced in a straightened out configuration. The device may have any number of hooks 20, such as three pairs of hooks. The number of hooks would preferably range from 6 to 12. The hooks assist in the retention of the device by resisting motion of the device in the vessel in a direction that would cause the hooks to engage the tissue. The hooks 20 do not have barbs so that the engagement is reversible by movement of the device opposite to the open end of the hook. Moreover, the hooks 20 may be configured to penetrate the wall of the LAA, but do not extend completely through the wall of the LAA. Thus, the hooks 20 reduce the incidence of effusion by not puncturing through wall of the LAA.

In one embodiment, the hooks 20 may be a part of the device—i.e., individual wires within the braided structure that are isolated, cut and a short portion of the wire adjacent the cut formed into an outward projecting wire or hook. The advantage of this configuration is that the device has a significantly lower profile since no added material (separate hooks) contributes to the collapsed configuration during passage through a catheter. In addition there are no added suture material or suture knots needed to attach hooks to the braided fabric, thus reducing the profile of the stent as well.

As explained above, the cylindrical shaped body portion 12 is adapted to be deployed within a vessel, cavity, or the like to be occluded, while the disk portion 14 is adapted to be positioned adjacent the wall surrounding the aperture associated with the vessel, cavity, or the like to be occluded. According to one embodiment, the device 10 extends from the proximal disk end clamp 16, radially outward to the disk maximum diameter A and back radially inward against itself to the transitional diameter H. The transitional diameter H extends distally a distance J whereby the device 10 forms a reverse cone toward the disk 14 with a diameter K where the device turns to follow parallel to the disk but spaced from the disk a distance E, radially outward to a diameter B. The device 10 continues to maintain a cylindrical diameter B distally a distance D. The device 10 may include a tapered surface of angle C, as shown in FIG. 1A, or not include a tapered surface as shown in FIGS. 4-6 and define a body portion 12 having a total length G. According to one embodiment, the distal end clamp 18 and the proximal end clamp 16 hold the braided wire ends from unraveling. However, it is understood that the device 10 may include an end clamp at its proximal and/or distal end. For example, the device 10 may include a proximal end clamp 16, while the distal end of the device is open. Furthermore, it is understood that the ends of the device 10 may be coupled using various techniques other than clamps, such as welding, bonding, fasteners, or the like. The proximal end clamp 16 also contains a threaded portion that reversibly connects to a delivery system (not shown) such as a cable or shaft with mating threads at its end. The proximal end clamp 16 and/or the distal end clamp 18 may be a radiopaque material, such as a platinum marker, for assisting a surgeon in positioning the device 10 within the vessel or body organ.

The improvement in disk flexibility and conformance to a wall of a vessel, body organ, or the like which are not perpendicular to the axis of the vessel, body organ, or the like to be occluded comes from the disk maximum diameter A in relation to the small diameter H, or the ratio of A/H. According to one embodiment, the ratio is in the range of 3 to 30, preferably about 10 to 25, and the ratio B/H is in the range of 2-25 and preferably 10-20. This ratio may reduce the bending force necessary to cause disk alignment to the wall of the vessel, body organ, or the like, or alternatively, alignment of the body portion to the vessel, body organ, or the like to be occluded. The transition diameter H has a length J which is about 2-5 times the diameter H. This length J may be necessary to allow a small dimension E between the disk inner surface and the body portion proximal end wall as shown in FIG. 1A. This may improve the device fit and the sealing of the device. To accommodate the length J of transition diameter H the device is shaped to form a conical surface at an angle L to the proximal end wall of the body portion. This conical surface may accommodate user displacement of the body portion from adjacent the disk by cone flattening and thereby provides increased radial expansive force for device retention on the proximal cylindrical outer diameter. Additionally, the conical surface may act as a spring to provide axial tension between the disk and body portion when they are displaced apart to keep the hooks 20 engaged in the wall of the vessel being occluded, thus improving device retention. In addition, the cylindrical portion may be purposely placed a spaced distance from the disk portion, as observed by angiography, to insure a retention force between the disk and cylindrical portions. The distance allows for more flexibility in placement of the cylindrical portion and adaptability to a wide range of anatomical conditions.

According to one embodiment, the difference in length between dimensions B and K and between dimensions D and J may be held constant for a variety of sizes of devices 10, while dimensions L and K may vary for different sizes of devices. According to another aspect of the present invention, the depth of the device (i.e., G+E) may be held constant for different sizes of devices 10. For example, the diameters B and A may be varied, while the depth G+E remains the same for both devices. One aspect of the present invention relating to a device for occluding the LAA includes a depth G+E of less than 10 mm.

The sizes of the body 12 and the disk 14 and device length can be varied as desired for differently sized vessels, channels, lumens, holes, cavities, or the like. A table of exemplary dimensional ranges and for select devices is provided below in mm. The exemplary dimensions provided below are given for a device 10 in its expanded, rest position, as the dimensions may change when deployed within the body (e.g., the length of the device may vary if the body member 12 is flexed with respect to the disk portion 14).

TABLE 1

|  | A | B | E | F | G | H | J | K | L |
|---|---|---|---|---|---|---|---|---|---|
| Range | 6 to 40 | 2 to 30 | 0 to 6 | 1 to 3 | 3 to 25 | 1 to 8 | 0 to 10 | 3 to 20 | 20 to 70 |
| LAA | 20 | 16 | 0.5 | 1.5 | 7 | 1.5 | 4 | 16 | 80 |
| LAA | 34 | 30 | 0.5 | 1.5 | 7 | 1.5 | 4 | 30 | 20 |

In reference to Table I, the device 10 having a diameter A of 20 mm is, in one embodiment, fabricated of 144 strands of 0.003 inch diameter Nitinol wire braided on an 18 mm diameter mandrel with a pick count of 40. After heat setting the 20 mm device 10 in its final molded shape, having hooks formed from the braid itself, the device may be collapsed for delivery through a delivery catheter 29 having a 7 French inside diameter and a 9 French outside diameter (3 French=1 mm).

With further reference to Table I, the device 10 having a diameter A of 34 mm is, in one embodiment, fabricated of 144 strands of 0.0045 inch diameter Nitinol wire braided on a 30 mm diameter mandrel with a pick count of 25. After heat setting the 34 mm device 10 in its final molded shape, having hooks formed from the braid itself, the device may be collapsed for delivery through a delivery catheter 29 having a 9 French inside diameter and a 11 French outside diameter.

The delivery system 28 shown in FIG. 2 can be used to urge the device 10 through the lumen of a catheter or long introducer sheath for deployment in the patient's body. The delivery system 28 can take any suitable shape, such as an elongated flexible metal shaft similar to a conventional guidewire or may be a hollow shaft. The delivery system 28 is used to advance the occlusion device 10 through the lumen 25 of a small diameter cylindrical tube, such as a delivery catheter 29 for deployment.

According to one embodiment, the device 10 is loaded into the lumen 25 by stretching the same to put it in an elongated condition. The device 10 may be inserted into the lumen 25 during the procedure or preassembled at a manufacturing facility, in that the devices of the present invention do not take on a permanent set when maintained in a compressed state. When the device is deployed out the distal end of the catheter, the device will still be retained by the delivery system. Once the proper position of the device 10 in the vessel, body organ, or the like is confirmed, the shaft of the delivery system 28 can be rotated about its axis to unscrew the clamp 16 from the threaded end of the delivery system. Of course the threaded connection could be at either end of the device depending on the anatomical situation and the desired or available means of access to the treatment site.

By keeping the device 10 attached to the delivery system, the operator may still retract the device back into a delivery sheath for repositioning if it is determined that the device is not properly positioned in the first attempt. In instances where the device 10 is improperly deployed on a first try, the device may be recovered by pulling the delivery system 28 proximally, thereby retracting the device back into the delivery catheter 29 prior to a second attempt at positioning the device relative to the vessel, body organ, or the like. The threaded attachment may also allow the operator to control the manner in which the device 10 is deployed out of the distal end of the delivery catheter. As explained below, when the device exits the delivery catheter it will tend to resiliently return to an expanded shape which was set when the fabric was heat treated. When the device springs back into this shape, it may tend to act against the distal end of the catheter, effectively urging itself forward beyond the end of the catheter. This spring action could conceivably result in improper positioning of the device. Since the threaded clamp 16 can enable the operator to maintain a hold on the device during deployment, the spring action of the device can be controlled and the operator can control the deployment to ensure proper positioning.

Optionally, the device 10 could be configured with a hollow inner clamp member 23 at both wire ends and an outer clamp proximal member 21 and a distal outer clamp member 26. The wire ends 24 are crimped between the inner and outer clamp members 21, 26 by swaging or alternatively may be bonded or welded between the clamp members. The inner clamp member is tubular and is sized with an inside diameter to freely pass a push wire 27. The distal outer clamp member 26 is sized with an inside diameter sufficient to accommodate the braid wire ends 24 surrounding the inner clamp member prior to swaging. The distal end on the distal outer clamp member 26 is solid (closed end) to accept the push force from the push wire 27 placed through both inner clamp members against this solid end. The proximal outer clamp member 21 is shown with external threads to reversibly connect to the delivery system 28, which may be an inner tube extruded of nylon block co-polymer such as Pebax with a 0.001 in. braided wire over the Pebax inner tube extrusion, followed by another outer layer of Pebax to cover the braid. The delivery catheter/sheath 29 may be similarly constructed except larger in diameter to accommodate the passage of the device 10 and delivery system 28. Such construction is typical in intravascular catheters where a flexibility and torque transmission are needed. Similar to the clamps 16, 18 above, the inner 23 and/or outer 26 clamp members may be a radiopaque material, such as a platinum marker, for assisting a surgeon in positioning the device 10 in the lumen.

According to one embodiment, the delivery catheter sheath 29 may have a 0.001 in thick inner layer of PTFE to lower friction for ease of device passage therethrough. The hollow delivery system sized to allow a push wire 27, made of stainless steel 0.008-0.014 in. to pass through the delivery system and the proximal clamp and to engage the distal clamp to push the distal clamp away from the proximal clamp to elongate the device, facilitate release of the hooks and facilitate recapture of the device into the delivery sheath 29. The distal end of the push wire 27 and the distal inner clamp 23 may be designed to attach by a threaded connection or other reversible means to ensure the wire does not inadvertently get positioned proximal to the distal inner clamp 23. By means of the delivery system 28 maintaining control of the proximal end of the device 10 and the push wire 27 being able to exert a push force on the distal end of the device, the device may be elongated or allowed to self expand and contract in length as desired. This aids in repositioning with the hooks being easily released by pushing on the push wire to force the device in the distal direction. This also aids in withdrawing the device back into the sheath 29 should the need occur, such as in incorrect device sizing to the anatomy. Although described as a push wire 27 for pushing on the distal end of the device, the push wire may be employed as a guide wire according to one embodiment. Thus, the push wire 27 may be configured to extend distally of the distal inner 23 and outer 26 clamp members, such that the device 10 may be delivered over-the-wire, as explained in further detail below. In this embodiment, the distal clamp member 26 is tubular with open ends and has a passageway therethrough sufficient for passage of the guidewire 27.

FIGS. 3A-C schematically illustrate how a medical device 10, generally as outlined above, can be used to occlude a vessel, channel, lumen, hole, cavity, or the like which is to be occluded. The device 10, may be collapsed and attached to the delivery system 28 such that the collapsed device can be passed through a delivery catheter 29 and that the distal end of the delivery catheter is adjacent the aperture 30 in the vessel wall 31 as shown in FIG. 3A. The delivery system 28 is advanced distally while holding back the delivery catheter 29 to urge the distal end of the device 10 out from the catheter 29 to elastically self expand substantially to its predetermined heat set molded state, whereby it contacts the vessel wall. At this point the distal end of catheter 29 may react to the expansion force and move proximally a small amount as shown in FIG. 3B. The hooks 20 begin to make contact with the vessel wall to hold the device in place. If needed to be positioned distally this can be done because the hooks will release in that direction. In FIG. 3C the device is full exited from the catheter 29 but still attached to the delivery system 28. As shown in this figure the disk 14 self aligns with the wall 31 by pivoting about the small diameter H. After the device is positioned as desired, the delivery system is disconnected by turning the delivery system 28 in a direction to release the threaded connection at the proximal end clamp 16.

Generally, a method in accordance with one embodiment of the present invention includes a method of treating a physiological condition of a patient. In accordance with this method, a medical device suitable for treating the condition, which may be substantially in accordance with one of the embodiments described in detail above, is selected. For example, if the LAA is to be occluded, the device 10 of FIGS. 1A, 1B, and 4 may be employed. The device 10 may be delivered and properly placed using two dimensional ICE, MRI, transesphogeal echocardiograpy, angiography, and/or Doppler color flow mapping. With the advent of two dimensional ICE, MRI, trans-esophageal echocardiography, bi-plane angiography, and Doppler color flow mapping, the approximate anatomy of the defect can be visualized. The device 10 that is employed will be based on the approximate size of the vessel, cavity, or the like to be occluded. Once the appropriate medical device is selected, a catheter may be positioned within a channel in patient's body to place the distal end of the catheter adjacent the desired treatment site, such as immediately adjacent or within the cavity of the LAA.

The medical device 10 can be collapsed into its collapsed configuration and inserted into the lumen of the catheter. The collapsed configuration of the device may be of any shape suitable for easy passage through the lumen of a catheter and proper deployment out the distal end of the catheter. For example, the devices shown in FIGS. 1A, 1B, 2, and 4-10 have a relatively elongated collapsed configuration wherein the devices are stretched along their axes for insertion into the catheter. This collapsed configuration can be achieved simply by stretching the device 10 generally along its axis, e.g., by manually grasping opposing ends of the device and pulling them apart, which will tend to collapse the body portion 12 and disk portion 14 of the device 10 inwardly toward the device's axis. In this regard, the device 10 is not unlike "Chinese handcuffs", which tend to constrict in diameter under axial tension.

The medical device 10 may also be collapsed by drawing the delivery system 28 coupled to the medical device proximally into an introducer tube (not shown) extending over the delivery system shaft. Drawing the delivery system 28 proximally pulls the device 10 into the introducer tube sized with an inside diameter to hold the medical device to a diameter to allow forward loading into the catheter 29.

Once the medical device 10 is collapsed and inserted into the catheter, it may be urged along the lumen of the catheter toward the distal end of the catheter. This may be accomplished by using a delivery system or the like removably connected to the device to urge it along the catheter. When the device begins to exit the distal end of the catheter, which is positioned adjacent the desired treatment site, it will tend to resiliently return substantially entirely to its preset expanded configuration. Superelastic alloys, such as Nitinol, are particularly useful in this application because of their ability to readily return to a particular configuration after being elastically deformed to a great extent. Hence, simply urging the medical device out of the distal end of the catheter tends to properly deploy the device at the treatment site.

Although the device will tend to resiliently return to its initial expanded configuration (i.e., its shape prior to being collapsed for passage through the catheter), it should be understood that it may not always return entirely to that shape. For example, the body member 12 of FIGS. 1A, 1B, 2, and 4-11 is intended to have a maximum outer diameter in its expanded configuration at least as large as and preferably larger than, the inner diameter of the lumen in which it is to be deployed. If such a device is deployed in a vessel, body organ, or the like having a small lumen, the lumen will prevent the device from completely returning to its expanded configuration. Nonetheless, the device would be properly deployed because it would engage the inner wall of the lumen to seat the device therein, as detailed above.

If the device is to be used to permanently occlude a channel in the patient's body, such as the devices 10 and 300 described above may be, one can simply disconnect the delivery system (example shown FIG. 6) by reversing the reversible connection to the device and retract the catheter and delivery system from the patient's body. This will leave the medical device deployed in the patient's vascular system so that it may occlude the blood vessel or other channel in the patient's body.

According to one embodiment, the device 10 may be implanted within the cavity of the LAA using an over-the-wire technique. When implanting the LAA transvascularly, the physician first accesses the right atrium via the femoral vein with a guidewire. A catheter may then be delivered over the guidewire and into the right atrium. A hollow needle shaft may then be placed over the guidewire, through the guidewire, and used to pierce the septum of the heart. After forming an opening through the septum, the guidewire may be advanced proximate to the LAA. The catheter may be moved through the opening in the septum via the guidewire and proximate to or within the LAA. The needle may then be removed, while the guidewire is left in position. The guidewire may then be removed and a delivery catheter having a device 10 constrained therein may be delivered proximate to the LAA. In the case of the device 10 having hollow proximal and distal end clamps 21, 23, 26 designed for passage of a guide wire therethrough, the guidewire may stay in place while the device is advanced over the guidewire.

The distal end of the catheter 29 may be placed partially within the LAA. The delivery catheter 29 may then be retracted proximally while holding the delivery system 28 stationary, which urges the body member 14 distally out of the delivery catheter 29, where it resiliently returns to its predefined expanded shape. The body member 12 expands to the diameter of the LAA but typically only extends partially within the depth of the LAA, as shown in FIG. 10. As the body member 12 expands, the hooks 20 are released from the catheter and engage the LAA to further fixate the device 10 therein. After fully released from the catheter 29, the delivery system 28 may be advanced to position the disk firmly against the atrium wall surrounding the ostium or opening of the LAA. According to one embodiment, radiopaque contrast media may be injected through the catheter 29 and into the left atrium to visualize on angiography whether the LAA is sealed from, or in communication with, the left atrium. Where layers of polyester fiber are positioned within each of the body portion 12 and disk portion 14, the contrast media typically resides between the layers of polyester fibers. If contrast media enters the LAA, but remains there after a predetermined period of time (e.g., less than 10 minutes), then communication with the left atrium is negligible and the position of the device 10 is adequate. Otherwise, the device 10 may need to be repositioned. Thus, the device 10 may be capable of substantially occluding the LAA in less than about 10 minutes such that no further visualization or monitoring of the LAA is needed. The device 10 may be disconnected by turning the delivery system 28 in a direction to release the threaded connection at the proximal end clamp 16. As shown in FIG. 10, the disk 14 self aligns with the wall of the LAA by pivoting about the transitional segment 19 such that the disk covers the opening of the LAA.

While a preferred embodiment of the present invention has been described, it should be understood that various changes, adaptations and modifications may be made therein without departing from the spirit of the invention and the scope of the appended claims. For example, it is anticipated that the body portion could be cylindrical, barrel shaped, concave, convex, tapered, or a combination of shapes without departing from the invention herein. Likewise the body portion distal and proximal ends could have differing shapes than the recessed conical shape described while still retaining the benefits described.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method of occluding a left atrial appendage ("LAA") of a patient with a medical device, the method comprising:
   accessing the patient's right atrium via a femoral vein;
   advancing a delivery catheter distally through an opening in a septum of a heart of the patient until a distal end of the delivery catheter is positioned proximate to the LAA or within the LAA;
   positioning the medical device within the delivery catheter in a collapsed condition, the medical device comprising:
      a self-expandable occluder body having a scaffolding structure formed of nitinol, the occluder body including an outer surface that tapers distally, the medical device having a proximal end portion and a substantially planar distal end portion, the distally tapering surface transitioning directly into the substantially planar distal end portion;
      a proximal end fastener coupled to the proximal end portion of the medical device, the proximal end fastener being threadedly coupled to a threaded member within the delivery catheter when the medical device is positioned within the delivery catheter in the collapsed condition;
      a distal end fastener coupled to the distal end portion of the medical device, the distal end fastener being radiopaque; and
      an occlusion material coupled to the scaffolding structure while the medical device is positioned within the delivery catheter in the collapsed condition,
   while the distal end of the delivery catheter is positioned proximate to the LAA or within the LAA, retracting the delivery catheter proximally relative to the threaded member to urge the occluder body out of the distal end of the delivery catheter;
   allowing the occluder body to self-expand within the LAA;
   piercing a wall of the LAA with a plurality of retentions hooks on the occluder body, each of the retention hooks having an end oriented toward the proximal end portion of the medical device;
   after piercing the wall of the LAA with the plurality of retention hooks, disconnecting the medical device from the threaded member by rotating the threaded member relative to the proximal end fastener to release the threaded connection between the medical device and the threaded member; and
   substantially fully occluding the LAA in less than about 10 minutes after allowing the occluder body to self-expand within the LAA,
   wherein the occluder body defines a recessed surface at a proximal wall of the occluder body such that, after the occluder body self-expands within the LAA, the recessed surface faces away from a cavity defined by the LAA and the proximal end fastener is positioned proximal to the recessed surface.

2. The method of claim 1, further comprising injecting radiopaque contrast media into a left atrium of the patient after the occluder body self-expands to visualize on angiography whether the LAA is sealed from, or in communication with, the left atrium.

3. The method of claim 2, further comprising determining that the LAA is in communication with the left atrium, and then repositioning the medical device within the LAA before disconnecting the medical device from the threaded member.

4. The method of claim 1, further comprising visualizing an approximate size of the LAA using trans-esophageal echocardiography prior to delivering the medical device to the LAA.

5. The method of claim 4, further comprising selecting a size of the medical device based on the visualized approximate size of the LAA.

6. The method of claim 1, wherein when the occluder body is urged out of the distal end of the delivery catheter, the distal end fastener deploys first from the delivery catheter.

7. The method of claim 1, wherein the proximal end fastener is radiopaque.

8. The method of claim 7, wherein the proximal end fastener and the distal end fastener are both formed of platinum.

9. The method of claim 1, wherein the distal end fastener has a passageway therethrough so that the medical device is configured for delivery over a guidewire.

10. The method of claim 1, wherein the plurality of retention hooks includes at least six retention hooks.

11. The method of claim 1, wherein the occlusion material is a layer of polyester.

12. The method of claim 1, wherein the substantially planar distal end portion has a diameter that is at least half of a diameter of the outer surface of the occluder body.

13. The method of claim 1, further comprising substantially fully occluding the LAA in less than about 5 minutes after allowing the occluder body to self-expand within the LAA.

14. The method of claim 1, wherein the proximal end portion of the medical device defines a proximal plane of occlusion.

15. The method of claim 1, wherein the scaffolding structure of the self-expandable occluder body is formed of a laser cut or etched tube of nitinol.

16. The method of claim 15, wherein the proximal end fastener is coupled to a plurality of wires of the scaffolding structure so that the plurality of wires are received within the proximal end fastener.

17. The method of claim 16, wherein the distal end fastener is coupled to a plurality of wires of the scaffolding structure at the distal end portion of the medical device so that the plurality of wires are received within the distal end fastener.

18. The method of claim 1, further comprising visualizing the radiopaque distal end fastener to assist in determining the position of the distal end fastener.

19. The method of claim 1, wherein the occlusion material is a layer of polyester, and the layer of polyester is sutured to the scaffolding structure.

20. The method of claim 19, wherein the layer of polyester is sutured to a circumference of the scaffolding structure.

* * * * *